United States Patent [19]

Ramachandran et al.

[11] Patent Number: 5,463,137
[45] Date of Patent: Oct. 31, 1995

[54] PROCESS FOR THE PRODUCTION OF OXO PRODUCTS

[75] Inventors: Ramakrishnan Ramachandran, Allendale; Loc H. Dao, Bound Brook, both of N.J.

[73] Assignee: The BOC Group, Inc., New Providence, N.J.

[21] Appl. No.: 231,546

[22] Filed: Apr. 22, 1994

Related U.S. Application Data

[63] Continuation-in-part of Ser. No. 129,527, Sep. 30, 1993, abandoned.

[51] Int. Cl.$^6$ .......................... C07C 45/50; C07C 51/14; C07C 29/14
[52] U.S. Cl. .......................... 568/454; 562/497; 562/517; 568/429; 568/438; 568/451; 568/492; 568/880; 568/882; 585/800; 585/809
[58] Field of Search .......................... 568/451, 454, 568/449, 429, 882, 492, 438; 562/497, 517; 585/800, 809

[56] References Cited

U.S. PATENT DOCUMENTS 4,917,711  4/1990  Xie et al. .......................... 55/68
5,001,274  3/1991  Bunning .......................... 568/454
5,087,763  2/1992  Sorensen .......................... 568/492
5,102,505  4/1992  Sorensen .......................... 568/492

FOREIGN PATENT DOCUMENTS 221128  5/1980  Germany.

Primary Examiner—Werren B. Lone
Attorney, Agent, or Firm—Coleman R. Reap; Larry R. Cassett

[57] ABSTRACT

A propylene stream which contains propane as an impurity is contacted with carbon monoxide and hydrogen in the presence of a hydroformylation catalyst thereby producing a product stream containing butyraldehyde and/or n-butyl alcohol, unreacted propylene and propane. A gas mixture containing propylene and propane is separated from the product stream and subjected to adsorption at a temperature of 0° to 250° C. in a bed of adsorbent which selectively adsorbs propylene, thereby adsorbing substantially all of the propylene from the gas mixture. The propylene is desorbed from the adsorbent and recycled to the reaction zone. The process is operated on a low per pass conversion with recycle of unreacted propylene. In the system of the invention the propylene adsorption unit may be upstream or downstream of the hydroformylation reactor.

29 Claims, 2 Drawing Sheets

0
PROCESS FOR THE PRODUCTION OF OXO PRODUCTS

RELATED CASE

This application is a continuation-in-part of application Ser. No. 129,527, filed Sep. 30, 1993, now abandoned.

FIELD OF THE INVENTION

The present invention is directed to a process for producing oxo products, and more particularly to a process in which propylene, carbon monoxide and hydrogen are reacted in the presence of a suitable catalyst to produce oxo products, such as butyraldehyde and n-butyl alcohol, and unreacted propylene is recycled to the reactor.

BACKGROUND OF THE INVENTION

Butyraldehyde is produced commercially by the hydroformylation reaction of propylene, carbon monoxide and hydrogen over a suitable catalyst. The reaction effluent is comprised of the butyraldehyde product, unreacted propylene, hydrogen and carbon monoxide, and small amounts of byproducts. Similarly, n-butyl alcohol is produced commercially by the hydroformylation-hydrogenation of propylene with carbon monoxide and hydrogen in the presence of a suitable catalyst. According to one commercial process for the production of butyraldehyde, the reaction is conducted on a semi-batch basis in the mixed gas-liquid phase in a stirred reactor at a temperature of about 130° C. and an absolute pressure of about 14 atmospheres. The reaction is strongly exothermic and part of the heat of reaction is removed by heat exchange and the remainder is used to evaporate the reaction products so that they can be easily removed from the reactor as a gas stream, thereby facilitating separation of the products and unreacted reactants from the catalyst residue. After exiting the reactor the gaseous product stream is cooled sufficiently to condense most of the butyraldehyde product. The noncondensed gas stream exiting the reactor, which include hydrogen, carbon monoxide, lower alkanes, including propylene and propane, and some of the butyraldehyde is conventionally recycled to the reactor. A small part of the recycle stream is purged from the system to prevent buildup of nonreactive components, such as the lower alkanes. The condensate is then stripped, preferably with steam, to remove residual volatiles (mostly propylene and propane) from the product stream. After cooling the gaseous stripper effluent to condense the steam, the volatiles stream is recycled to the reactor.

A significant disadvantage encountered in the above-described process results from the fact that industrial grade propylene usually contains small amounts, for example up to about 10% by volume, propane. Since propane is not generally affected by hydroformylation catalysts, the effluent stream usually contains propane, and the amount of propane present in the effluent may be significant, particularly when low purity propylene is used as feed. In such cases a significant volume of the volatiles must be purged to prevent buildup of propane in the system. Unfortunately, some propylene and butyraldehyde are also discharged from the system in the purge stream.

Because of the difficulty of separating propylene from propane, efficient operation of propylene recycle hydroformylation processes is hard to achieve when the propylene feed contains propane as an impurity. Continuous efforts are underway to enhance the efficiency of recycle butyraldehyde hydroformylation processes, including research investigations for improved procedures for separating propane from propylene prior to recycling the propylene to the reactor. The present invention provides such an improved procedure.

SUMMARY OF THE INVENTION

The present invention is a recycle process for producing oxo products, such as butyraldehyde, by hydroformylating propylene which contains propane as an impurity with carbon monoxide and hydrogen to produce butyraldehyde. The recycle process can also be used to produce n-butyl alcohol by hydroformylating and hydrogenating propane to produce the alcohol. The resulting product stream containing the desired oxo product, unreacted propylene and propane, and perhaps unreacted carbon monoxide and hydrogen is removed from the reactor in the vapor state. Propane can then be removed from part or all of the noncondensed portion of the product stream by pressure swing adsorption in one or more steps and the propane-depleted stream or streams are then recycled to the reactor.

According to a first embodiment of the invention, propylene which contains propane as an impurity, hydrogen and carbon monoxide are introduced into a reaction vessel and contacted therein with a hydroformylation catalyst, or a hydroformylation-hydrogenation catalyst, thereby producing a gaseous product stream comprising mixed butyraldehydes or mixed butyraldehydes and n-butyl alcohol, unreacted propylene, propane and, usually, unreacted carbon monoxide and hydrogen. The product stream is then cooled in a product condenser to produce a condensate which contains most of the butyraldehydes or mixed butyraldehydes and n-butyl alcohol, and some propylene and propane. In addition to the condensate, a gas stream comprised of the noncondensable components of the product stream, i.e. carbon monoxide and hydrogen, and some propylene, propane and butyraldehydes is produced. The condensate is next flashed and/or stripped, preferably with steam, thereby evaporating propylene and propane from the condensate. The remaining portion of the condensate, now comprised substantially of butyraldehydes or mixed butyraldehydes and n-butyl alcohol, and perhaps small amounts of heavier byproducts, is sent to product recovery for further purification. The vapor phase, which contains propylene, propane and steam, if steam stripping is employed, is cooled to condense the steam, thereby producing a gas stream rich in propylene and propane.

The gas streams from the product condenser and the flash chamber or steam condenser in the above embodiment can be treated in a number of ways. According to a first aspect, all or part of the gas stream from the product condenser and all or part of the gas stream from the flash chamber/steam condenser are subjected to adsorption, thereby adsorbing propylene from the gas stream. The nonadsorbed propane-containing component is discharged from the system and the adsorbed propylene-rich component is recycled to the reactor.

According to a second aspect, the entire gas stream from the steam condenser is recycled to the reactor and all or part of the gas stream from the product condenser is subjected to adsorption to adsorb propylene from this gas stream. The nonadsorbed propane-containing component is discharged from the system and the adsorbed propylene-rich component is recycled to the reactor.

According to a third, and most preferred aspect, the entire gas stream from the product condenser is recycled to the reactor and all or part of the gas stream from the flash chamber/steam condenser is subjected to adsorption to adsorb propylene from this gas stream. The nonadsorbed propane-rich component is discharged from the system and the adsorbed propylene-rich component is recycled to the reactor.

In the adsorption system part or all of the propylene in the gas stream is separated from the propane by pressure swing adsorption or by temperature swing adsorption in one or more adsorption vessels containing beds of adsorbent which selectively adsorb alkenes from gas mixtures containing alkenes and alkanes. The adsorption process is operated under conditions which result in the production of an adsorbed stream enriched in propylene and a non-adsorbed product stream enriched in propane, and is preferably operated to retain substantially all of the unreacted propylene in the product gas stream and reject most of the propane in the stream. The propylene-enriched gas stream obtained upon desorption of the adsorption beds is recycled to the reaction vessel.

In a second embodiment of the invention a propylene-propane gas mixture is subjected to pressure swing adsorption or temperature swing adsorption in beds of adsorbent which selectively adsorb alkenes from gas mixtures containing alkenes and alkanes, as described above, to produce a propylene-enriched stream. The propylene-enriched stream and hydrogen and carbon monoxide are introduced into the reaction vessel and contacted therein with a hydroformylation catalyst, or a hydroformylation-hydrogenation catalyst, thereby producing the gaseous product stream comprising butyraldehydes or butyraldehydes-n-butyl alcohol mixture, unreacted propylene, propane and perhaps carbon monoxide and hydrogen. The product stream is then cooled in a product condenser to produce a condensate containing most of the butyraldehydes or butyraldehydes-n-butyl alcohol mixture, and some propylene and propane, and a gas stream comprised of carbon monoxide and hydrogen and some propylene, propane and butyraldehydes. The condensate is flashed and/or stripped with steam, as described above, thereby evaporating propylene and propane from the condensate. The condensate, now comprised substantially of butyraldehydes or mixed butyraldehydes and n-butyl alcohol, and perhaps small amounts of heavier byproducts, is sent to product recovery for further purification. The vapor phase, now rich in propylene and propane and perhaps containing steam, is cooled to condense the steam (if steam stripping is employed).

In the second embodiment of the invention the gas stream from the product condenser and the vapor phase from the flash chamber and/or steam stripper are also treated according to one of the three recycle-adsorption aspects described above.

The adsorption step of the above-described embodiments of the invention is typically carried out at a temperature in the range of about 0° C. to about 250° C., and is preferably carried out at a temperature of at least about 50° C. The adsorption step is generally carried out at an absolute pressure in the range of about 0.2 to 100 bar, and is preferably carried out carried out at an absolute pressure of about 1 to 50 bar.

In a preferred embodiment of the invention, the adsorbent is a type A zeolite, and in the most preferred embodiment, it is type 4A zeolite.

In other preferred embodiments of the invention the adsorption bed regeneration step is effected by vacuum means or by purging the bed with one or more of an inert gas, the nonadsorbed gas product from the adsorption system or the adsorbed product gas from the adsorption system, or by combinations of vacuum and purge regeneration; and bed repressurization is effected using the propylene-enriched desorbed gas from the adsorption system.

DETAILED DESCRIPTION OF THE INVENTION

The invention can be better understood from the accompanying drawings in which the same reference letters or numerals are used to designate the same or similar pieces of equipment in different figures. Auxiliary equipment, including compressors, heat exchangers and valves, not necessary for an understanding of the invention, have been omitted from the drawings to simplify discussion of the invention.

The process of the invention can be used to produce oxo products, such as butyraldehyde, butyl alcohol and butyric acid by reacting propylene with carbon monoxide and hydrogen in the presence of an appropriate catalyst. For purposes of illustration however, the invention will be described in particular as it applies to the manufacture of butyraldehyde.

Figure 1:
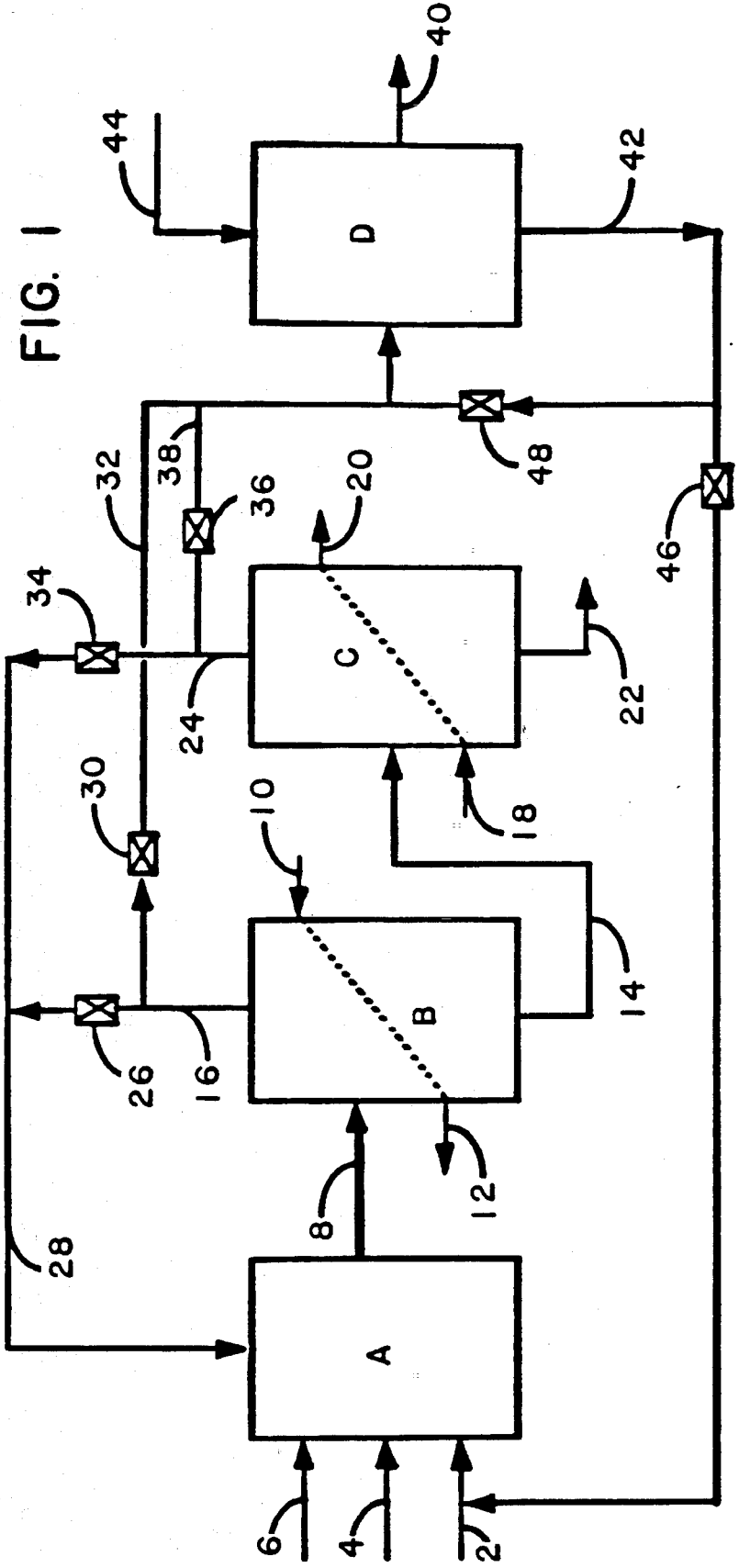
FIG. 1 illustrates, in a block diagram, one embodiment of a system for producing butyraldehyde in accordance with the present invention.

In the system of FIG. 1 unit A is a reaction vessel, unit B is a condenser, unit C is a butyraldehyde product recovery unit and D is a propylene separator. Considering FIG. 1 in greater detail, a feed stream comprising at least 90 weight percent and preferably at least 95 weight percent propylene, the balance being substantially propane, is introduced into reactor A through line 2. Carbon monoxide and hydrogen are introduced into reactor A through feed lines 4 and 6, respectively. If desired the carbon monoxide and hydrogen may be introduced together, which is convenient when these components comprise a syngas. The catalyst and any other desired additives may be introduced into reactor A either with one of the feed streams or separately through feed lines not shown in FIG. 1. The predominant reaction taking place in reactor A proceeds according to the equation:

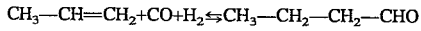

$$CH_3-CH=CH_2+CO+H_2 \leftrightarrows CH_3-CH_2-CH_2-CHO$$

Reactor A may be any conventional reactor in which the hydroformylation of propylene is carried out, either on a batch or a continuous basis. The reactor is generally provided with stirring means and cooling means to ensure a uniform and controlled reaction. The reactants contact the catalyst in reactor A at a suitable temperature and pressure and a portion of the propylene is hydroformylated to butyraldehydes. The details of the hydroformylation reaction are well known and form no part of the present invention. Typically, the reaction is conducted at temperatures in the range of about 100° to about 175° C., and at pressures in the range about 10 to about 20 atmospheres. Hydroformylation catalysts suitable for use in the reaction include rhodiumtriphenylphosphine complex and rhodiumtrisulfophenylphosphine complex. Typical hydroformylation processes are the Union Carbide/Davy-Mckee/Johnson-Matthey process using an oil-soluble rhodiumtriphenylphosphine catalyst complex, and the Ruhrchemie/Rhone-Poulenc process using a water-soluble rhodiumtrisulfophenylphosphine catalyst complex. If it is desired to produce n-butyl alcohol, the alcohol, together with butyraldehyde, is produced by the reaction of propylene, carbon monoxide and hydrogen in the presence of a cobalt hydrocarbonyl catalyst. These processes are well known and form no part of the present invention.

Due to the highly exothermic nature of the hydroformylation reaction, the butyraldehyde product, unreacted propylene, carbon monoxide and hydrogen, and the propane impurity that entered the reactor with the propylene feed stream are all gaseous and thus can be easily separated from the catalyst residue and solvent present in the reactor. These gaseous components leave reactor A through line 8 and are transported to product condenser B.

Product condenser B can be any suitable condenser, and it is generally of the vertical tube and shell design. A coolant, such as cold water, enters condenser B through line 10, passes through the tubes of the condenser and exits condenser B through line 12. The hot gaseous stream entering condenser B through line 8 contacts the outside surfaces of the heat exchange tubes and most of the higher boiling components of the gas stream (butyraldehydes or mixed butyraldehydes-n-butyl alcohol and higher molecular weight byproducts) and some propylene and propane condense and drop to the bottom of the condenser and are removed therefrom through line 14. A noncondensed gas stream, containing the permanent gases, including carbon monoxide, and hydrogen, some propylene and propane and some of the higher boiling components mentioned above, rises to the top of product condenser B and leaves the condenser line 16.

The condensate stream leaving condenser B through line 14 next enters product recovery unit C. Unit C may be a flash chamber or a stripping vessel or it may comprise both a flash chamber and a stripping vessel. When Unit C is a flash chamber, separation of the volatile components from the remaining contents of the reactor effluent is accomplished by heating the contents in unit C, preferably at reduced pressure. The heating can be provided by, for example, electric or steam heating means (not shown). When unit C is a stripper the volatile components in the stream being treated are evaporated by directly passing a hot fluid, such as steam or heated nitrogen through the contents of the stripper, preferably while stirring the contents. It is preferable to use steam as the stripping gas since it can be easily separated from the gaseous effluent from the stripper by cooling the effluent and condensing the steam. In the system illustrated in FIG. 1 unit C represents a flash chamber and in the FIG. 2 system, described in detail below, unit C represents a steam stripper.

Unit C is typically equipped with agitating means (not shown). The contents of unit C are heated indirectly by steam which enters unit C through line 18, condenses in the heating coils in unit C and exits this unit as steam condensate through line 20. Product condensate from condenser B passes through line 14 and into unit C wherein it is heated sufficiently to evaporate the propylene and propane contained in the condensate with minimal evaporation of the butyraldehyde product. The butyraldehyde product leaves flash chamber C through line 22 and is sent to downstream facilities for product purification and further processing. The propylene-propane gas mixture passes out of unit C through line 24.

Valve 26 controls flow of gas through line 16, which, together with line 28, affords recycle of gas from condenser B to reactor A. Valve 30, located in line 32, controls flow of gas from condenser B to separator D. Valve 34, located in line 24, controls flow of recycle gas from flash chamber C to reactor A via lines 24 and 28. Valve 36, located in line 38 controls flow of gas from flash chamber C to separator D.

As mentioned above, separator D is a pressure swing adsorption system or a temperature swing adsorption system. It may comprise a single adsorption bed or a battery of beds arranged in series or parallel or in combinations of these. In preferred plants separator D comprises two or more adsorbent beds cycled out of phase to provide a pseudo-continuous recycle of unreacted propylene to reactor A. Preferred plants comprise two or more beds operated in a cyclic process comprising adsorption at a relatively high temperature and pressure and desorption or bed regeneration at a relatively low pressure or vacuum, in the case of pressure swing adsorption, and at a temperature higher than the adsorption temperature, in the case of temperature swing adsorption.

The function of separator D is to adsorb unreacted propylene from the feed streams to this unit, the compositions of which will vary depending upon which stream or streams are sent to this unit, but which generally contain unreacted propylene and propane, other light components and possibly some product in gaseous form (and the stripping gas, when this gas is noncondensable). As the gaseous effluent from unit C passes through separator D, substantially all of the unreacted propylene is adsorbed by the propylene-selective adsorbent contained therein. The nonadsorbed gases leave separator D through waste gas discharge line 40. When the unreacted propylene front reaches a predetermined point in separator D, the flow of feed to the particular adsorption unit or units in service is terminated and the regeneration phase of the cycle is begun.

The method or regeneration of the adsorption beds depends upon the type of adsorption process employed. In the case of pressure swing adsorption, the regeneration phase generally includes a countercurrent depressurization step during which the beds are vented countercurrently until they attain atmospheric pressure. If desired the beds may be further depressurized by evacuation to subatmospheric pressure by means of a vacuum inducing device, such as a vacuum pump (not shown). In either case the propylene desorbed from the beds is recycled to reactor A via line 42.

In some cases, in addition to the countercurrent depressurization step(s), it may be desirable to purge the bed with an inert gas or one of the gas streams exiting separator D. In this event the purge step is usually initiated towards the end of the countercurrent depressurization step, or subsequent thereto. During this step, a nonadsorbable purge gas is introduced into separator D via line 44 and passed countercurrently through the adsorbent beds, thereby forcing desorbed propylene out of separator D through line 42. The purge gas may be nonadsorbed product gas exiting separator D through line 40 or a nonadsorbable gas obtained from a different source, such as an inert permanent gas like nitrogen.

When the system of FIG. 1 is operated in accordance with the first aspect of the first embodiment mentioned above, valves 30 and 36 are open and valves 26 and 34 may be open or closed. In this aspect some or all of the gases exiting condenser B and flash chamber C are transported to separator D through lines 32 and 38, respectively. If all of the gases from condenser B and flash chamber C are sent to separator D, then both valves 26 and 34 are closed. However if only part of the gas from condenser B is sent to separator D and the remainder is recycled to reactor A, then valve 26 will be open. Similarly if only part of the gas from flash chamber C is sent to separator D and the remainder is recycled to reactor A, then valve 34 will be open.

When the system of FIG. 1 is operated in accordance with the second aspect mentioned above, valves 30 and 34 will be open and valve 36 will be closed. Valve 26 may be closed or open depending on whether all or only part of the gas from flash chamber C is sent to separator D.

When the system of FIG. 1 is operated in accordance with the third aspect mentioned above, valves 26 and 36 will be open and valve 30 will be closed. Valve 34 may be closed or open depending on whether all or only part of the gas from flash chamber C is sent to separator D. This is the preferred aspect of the embodiment of FIG. 1, since the gas stream processed in separator D will comprise mostly propylene and propane. When the system is operated efficiently this alternative will effectively prevent the buildup of propane in the system and permit conversion of substantially all of the propylene entering the system to butyraldehyde and/or n-butyl alcohol.

In an alternative mode of operation of the system of FIG. 1 the propylene desorbed from separator D during the countercurrent depressurization step(s) is recycled through line 42 and valve 46 and back to reactor A, and all or a portion of the purge gas and propylene desorbed from the bed during the purge step is recycled to separator D for reprocessing through the adsorption system. This is accomplished by keeping valve 46 open and valve 48 closed during at least part of the countercurrent depressurization step, and closing valve 46 and opening valve 48 at the point during that part of the purge step when it is desired to recycle the purge gas-propylene mixture directly to the feed inlet of separator D. The advantage of this embodiment is that it permits the amount of purge gas that is recycled to the reactor to be minimized.

The adsorption cycle may contain steps other than the fundamental steps of adsorption and regeneration. For example, it may be advantageous to depressurize the adsorption bed in multiple steps, with the first depressurization product being used to partially pressurize another bed in the adsorption system. This will further reduce the amount of gaseous impurities recycled to reactor A. It may also be desirable to include a cocurrent purge step between the adsorption phase and the regeneration phase. The cocurrent purge is effected by terminating the flow of feed gas into separator D and passing high purity propylene cocurrently into the adsorption bed at adsorption pressure. This has the effect of forcing nonadsorbed gas in the void spaces in separator D toward the nonadsorbed gas outlet, thereby ensuring that the propylene produced during the countercurrent depressurization will be of high purity. The high purity propylene used for the cocurrent purge can be obtained from an intermediate storage facility in line 42 (not shown), when separator D comprises a single adsorber; or from another adsorber that is in the adsorption phase, when separator D comprises multiple adsorbers arranged in parallel and operated out of phase; or from propylene feed line 2.

The adsorbent in separator D may be any adsorbent which selectively adsorbs alkenes from a gas mixture containing the alkenes and one or more alkanes. In general, the adsorbent may be alumina, silica, zeolites, carbon molecular sieves, etc. Typical adsorbents include alumina, silica gel, carbon molecular sieves, zeolites, such as type A and type X zeolite, etc. The preferred adsorbents are type A zeolites, and the most preferred adsorbent is type 4A zeolite.

Type 4A zeolite, i.e. the sodium form of type A zeolite, has an apparent pore size of about 3.6 to 4 Angstrom units. This adsorbent provides enhanced selectivity and capacity in adsorbing ethylene from ethylene-ethane mixtures and propylene from propylene-propane mixtures at elevated temperatures. This adsorbent is most effective for use in the invention when it is substantially unmodified, i.e. when it has only sodium ions as its exchangeable cations. However, certain properties of the adsorbent, such as thermal and light stability, may be improved by partly exchanging some of the sodium ions with other cations. Accordingly, it is within the scope of the preferred embodiment of the invention to use a type 4A zeolite in which some of the sodium ions attached to the adsorbent are replaced with other metal ions, provided that the percentage of ions exchanged is not so great that the adsorbent loses its type 4A character. Among the properties that define type 4A character are the ability of the adsorbent to selectively adsorb ethylene from ethylene-ethane mixtures and propylene from propylene-propane gas mixtures at elevated temperatures, and to accomplish this result without causing significant oligomerization or polymerization of the alkenes present in the mixtures. In general, it has been determined that up to about 25 percent (on an equivalent basis) of the sodium ions in 4A zeolite can be replaced by ion exchange with other cations without divesting the adsorbent of its type 4A character. Cations that may be ion exchanged with the 4A zeolite used in the alkene-alkane separation include, among others, potassium, calcium, magnesium, strontium, zinc, cobalt, silver, copper, manganese, cadmium, aluminum, cerium, etc. When exchanging other cations for sodium ions it is preferred that less than about 10 percent of the sodium ions (on an equivalent basis) be replaced with such other cations. The replacement of sodium ions may modify the properties of the adsorbent. For example, substituting some of the sodium ions with other cations may improve the stability of the adsorbent.

Another class of preferred adsorbents are those which contain certain oxidizable metal cations, such as copper-containing adsorbents, which possess enhanced adsorptive capacity and selectivity with respect to the preferential adsorption of alkenes from gaseous alkene-alkane mixtures. Suitable adsorbent substrates for manufacturing copper-modified adsorbents include silica gel, and zeolite molecular sieves, such as zeolite type 4A, zeolite type 5A, zeolite type X and zeolite type Y. The manufacture and use of copper-modified adsorbents and examples of suitable copper-containing adsorbents are set forth in U.S. Pat. No. 4,917,711, the disclosure of which is incorporated herein by reference.

The temperature at which the adsorption step is carried out depends upon a number of factors, such as the particular adsorbent being used, e.g. unmodified 4A zeolite, a particular metal-exchanged 4A zeolite or another adsorbent which selectively adsorbs alkenes from alkene-alkane mixtures, and the pressure at which the adsorption is carried out. In general, the adsorption step is carried out at a minimum temperature of about 50° C. and is preferably carried out at a temperature of at least about 70° C. The upper temperature limit at which the adsorption step in unit A is carried out is determined mostly by economics. In general the adsorption step can be carried out at a temperature below the temperature at which the alkene undergoes chemical reaction, such as polymerization. When unmodified 4A zeolite is used as the adsorbent the reaction is generally carried out at or below 250° C., and is preferably carried out at a temperature at or below 200° C. Oxidizable metal-containing adsorbents, such as copper modified adsorbents, are particularly effective at temperatures above about 100° C., for example at temperatures between about 100° C. and 250° C. They are preferably used at temperatures in the range of about 110° to 200° C., and most preferably at temperatures in the range of about 125° to about 175° C.

The pressures at which the adsorption and regeneration steps of the pressure swing adsorption embodiment of the invention are carried out are not critical, and in general, these steps can be carried out at any of the usual pressures employed for gas adsorption processes, with the limitation, of course, that the adsorption step be carried out at a pressure greater than the regeneration step pressure. Typically, when the adsorption process is pressure swing adsorption the absolute pressure during the adsorption step will range generally from about 0.2 to about 20 atmospheres, and preferably from about 1 to 10 atmospheres, and during the regeneration step will range from about 20 millibar to about 1 atmosphere or more. When the adsorption process is temperature swing adoption the pressure during both adsorption and desorption is desirably atmospheric or near atmospheric.

Figure 2:
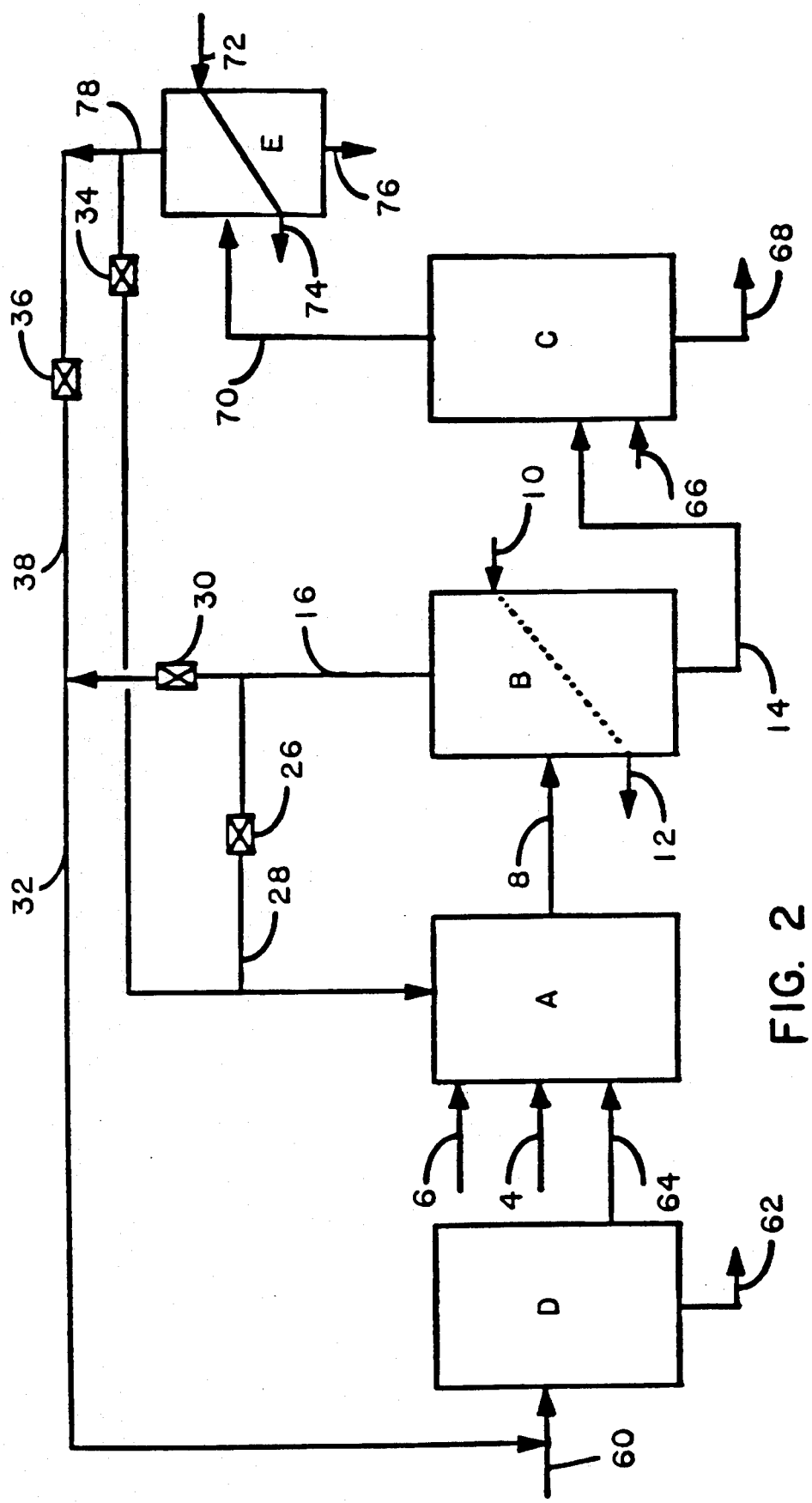
FIG. 2 illustrates, in a block diagram, an alternate embodiment of the system illustrated in FIG. 1.

FIG. 2 illustrates an alternate embodiment of the invention described with reference to FIG. 1. In the FIG. 2 embodiment separator D is positioned upstream of reactor A. Except for the fact that separator D of FIG. 2 may be larger than separator D of FIG. 1, equipment units A, B and D of FIGS. 1 and 2 are substantially identical. As mentioned above, unit C of FIG. 2 represents a gas stripping unit. Unit E is a steam condenser.

In practicing the process of the invention in the system of FIG. 2, a feed stream comprised substantially of propylene, but containing propane as an impurity, is introduced into separator D through line 60. The feed stream is subjected to pressure swing adsorption or temperature swing adsorption in separator D, as described above. Nonadsorbed propane-enriched product is discharged from separator D through line 62 and desorbed propylene-enriched product is recovered from unit D through line 64. The propylene-enriched product next enters reactor A wherein the propylene reacts with the carbon monoxide and hydrogen entering reactor A through lines 4 and 6, respectively, to form butyraldehyde and/or n-butyl alcohol under the conditions set forth above. The reaction product is discharged from reactor A through line 8 and it next enters condenser B, wherein noncondensed gases are separated from the condensed reaction product, as described above. These gases are removed from unit B through line 16 and recycled to reactor A or transported to separator D, as described below. The condensate from condenser B is forwarded to stripper C through line 14. In unit C the condensate is stripped with steam, which enters this unit through line 66, thereby vaporizing substantially all of the propylene and propane contained in the condensate. The degassed condensate leaves stripper C through line 68 and is sent to downstream units for product recovery and further processing. The stripped propylene and propane and the steam exit unit C through line 70 and next enter steam condenser E. The steam in the vapor stream is condensed in condenser E by a cooling medium, such as water, which enters unit E through line 72 and exits this unit through line 74. The steam condensate is removed from condenser E through line 76 and returned to the steam regenerating means, and the propylene-propane gas stream passes out of unit E through line 78. All or a portion of the recovered propylene-propane gas stream is recycled to separator D or reactor A, as described below.

When the system of FIG. 1 is operated in accordance with the first aspect of the second embodiment mentioned above, valves 30 and 36 are open and valves 26 and 34 may be open or closed. In this aspect some or all of the gases exiting condenser B and steam condenser E are transported to separator D through lines 16, 38 and 32. If all of the gases from condenser B and steam condenser E are sent to separator D, then both valves 26 and 34 are closed. However if only part of the gas from condenser B is sent to separator D and the remainder is recycled to reactor A, then valve 26 will be open. Similarly if only part of the gas from steam condenser E is sent to separator D and the remainder is recycled to reactor A, then valve 34 will be open.

When the system of FIG. 2 is operated in accordance with the second aspect mentioned above, valves 30 and 34 will be open and valve 36 will be closed. Valve 26 may be closed or open depending on whether all or only part of the gas from flash chamber C is sent to separator D.

When the system of FIG. 2 is operated in accordance with the third aspect mentioned above, valves 26 and 36 will be open and valve 30 will be closed. Valve 34 may be closed or open depending on whether all or only part of the gas from flash chamber C is sent to separator D. As was the case with the embodiment of FIG. 1, this is the preferred aspect of the embodiment of FIG. 2, since the gas stream processed in separator D will comprise mostly propylene and propane.

It will be appreciated that it is within the scope of the present invention to utilize conventional equipment to monitor and automatically regulate the flow of gases within the system so that it can be fully automated to run continuously in an efficient manner.

Important advantages of the invention are that it permits use of a less pure propylene feed stream than was formerly possible, and the process can be run at a relatively low per pass conversion of the propylene feed to the desired product, thereby achieving substantially improved selectivity. It will be appreciated that a system that achieves enhanced selectivity, and hence increased overall yield of a desired product, is highly beneficial.

The invention is further illustrated by the following example in which, unless otherwise indicated, parts, percentages and ratios are on a volume basis.

EXAMPLE I

This example is a hypothetical example depicting the production of butyraldehyde using as feed to the reactor a propylene stream containing propane as an impurity, carbon monoxide and hydrogen. The proposed propylene feed stream is comprised of 95.0% propylene and 5.0% propane. The ratio of carbon monoxide to propylene feed is 0.46 to 1 and the ratio of hydrogen to propylene is 2.0 to 1. The proposed reaction system is similar to the system illustrated in FIG. 1. except that the reactor effluent is separated into a gas phase and a condensate phase in a product condenser, and part of the gas phase is recycled to the butyraldehyde reactor and the remainder is subjected to a pressure swing adsorption process using zeolite type 4A as adsorbent. The butyraldehyde reactor is to be operated at a temperature of 130° C. and an absolute pressure of 14 atmospheres. The adsorption process is to be carried out at an adsorption pressure of 0.7 bar and a bed regeneration pressure of 300 mbar.

The results of the run are recorded in the Table. In the Table, stream 1 is the fresh feed flow to the system; stream 2 is the combined total of the fresh feed flow and the flows of all recycle streams to the reactor; stream 3 is the flow of reactor effluent to the product condenser; stream 4 is the flow of condensed product from the product condenser; stream 5 is the total flow of gas phase from the product condenser; stream 6 is the flow of gas recycled from the product condenser directly to the reactor; stream 7 is the flow of gas from the product condenser to the pressure swing adsorption system; stream 8 is the flow of desorbed recycle gas from the pressure swing adsorption system to the reactor; and stream 9 is the flow of waste gas from the pressure swing adsorption system.

TABLE I

| COMPONENT | SEL. | STREAM | | | | | | | | |
|---|---|---|---|---|---|---|---|---|---|---|
| | | 1 moles | 2 moles | 3 moles | 4 moles | 5 moles | 6 moles | 7 moles | 8 moles | 9 moles |
| Propylene | | 112.939 | 719.647 | 609.757 | 0.000 | 609.757 | 548.781 | 60.976 | 57.927 | 3.049 |
| Propane | 0.004 | 5.944 | 79.736 | 80.208 | 0.000 | 80.208 | 72.188 | 8.021 | 1.604 | 6.417 |
| CO | | 130.198 | 328.159 | 218.741 | 0.000 | 218.741 | 196.867 | 21.874 | 1.094 | 20.780 |
| H$_2$ | | 235.093 | 1432.314 | 1322.896 | 0.000 | 1322.896 | 1190.606 | 132.290 | 6.614 | 125.675 |
| Methane | | 7.946 | 88.290 | 88.290 | 0.000 | 88.290 | 79.461 | 8.829 | 0.883 | 7.946 |
| i-Butyraldehyde | 0.076 | 0.000 | 2.659 | 8.352 | 5.679 | 2.673 | 2.405 | 0.267 | 0.254 | 0.013 |
| n-Butyraldehyde | 0.910 | 0.000 | 24.278 | 100.000 | 75.600 | 24.400 | 21.960 | 2.440 | 2.318 | 0.122 |
| Trimer | 0.005 | 0.000 | 0.000 | 0.168 | 0.168 | 0.000 | 0.000 | 0.000 | 0.000 | 0.000 |
| Tetramer | 0.000 | 0.000 | 0.000 | 0.005 | 0.005 | 0.000 | 0.000 | 0.000 | 0.000 | 0.000 |
| Aldol | 0.005 | 0.000 | 0.000 | 0.269 | 0.269 | 0.000 | 0.000 | 0.000 | 0.000 | 0.000 |
| Total | 1.000 | 492.120 | 2675.083 | 2428.688 | 81.722 | 2346.966 | 2112.269 | 234.697 | 70.694 | 164.003 |

Although the invention has been described with particular reference to specific experiments, these experiments are merely exemplary of the invention and variations are contemplated. For example, the process of the invention can be practiced in equipment arrangements other than those illustrated in the drawings. The scope of the invention is limited only by the breadth of the appended claims.

We claim:

1. A process for the production of an oxo product selected from butyraldehyde, n-butyl alcohol, butyric acid and mixtures of these comprising the steps:

(a) contacting a propylene stream containing propane as an impurity with carbon monoxide and hydrogen in a reaction zone in the presence of a hydroformylation catalyst under conditions which result in the production of a product stream comprising the oxo product, unreacted propylene and propane;

(b) separating a gas stream comprising unreacted propylene and propane from said product stream;

(c) selectively adsorbing propylene from said gas stream by passing said gas stream through an adsorption zone containing an adsorbent which selectively adsorbs propylene;

(d) regenerating said adsorbent, thereby producing a propylene-enriched gas stream; and (e) recycling at least part of said propylene-enriched gas stream to said reaction zone.

2. The process of claim 1, wherein step (b) is carried out by flashing unreacted propylene and propane from said product stream.

3. The process of claim 1, wherein step (b) is carried out by stripping unreacted propylene and propane from said product stream.

4. The process of claim 1, wherein step (b) is carried out by first flashing unreacted propylene and propane from said product stream and then stripping unreacted propylene and propane from said product stream.

5. The process of claim 1, further comprising, prior to step (b), the step of separating from said product stream a gas stream containing at least one member selected from carbon monoxide and hydrogen.

6. The process of claim 1, wherein a first portion of said propylene-enriched gas stream is recycled to said reaction zone and a second portion of said propyleneenriched gas stream is recycled to said adsorption zone.

7. A process for the production of an oxo product selected from butyraldehyde, n-butyl alcohol, butyric acid and mixtures of these comprising the steps:

(a) selectively adsorbing propylene from a propylene-propane gas mixture by passing said gas mixture through an adsorption zone containing an adsorbent which selectively adsorbs propylene;

(b) regenerating said adsorbent, thereby producing propylene-enriched gas;

(c) contacting said propylene-enriched gas with carbon monoxide and hydrogen in the presence of a hydroformylation catalyst in a reaction zone under conditions which result in the production of a product stream containing the desired oxo product, unreacted propylene and propane;

(d) separating unreacted propylene and propane from said product stream; and (e) recycling said unreacted propylene and propane to said adsorption zone.

8. The process of claim 1 or claim 7, wherein the adsorption step is conducted at a temperature above about 50° C.

9. The process of claim 1 or claim 7, wherein the adsorption step is conducted at a temperature in the range of about 50° to about 250° C.

10. The process of claim 1 or claim 7, wherein the adsorbent is selected from alumina, type 4A zeolite, type 5A zeolite, type 13X zeolite, type Y zeolite and mixtures of these.

11. The process of claim 9, wherein the adsorbent contains an oxidizable metal ion.

12. The process of claim 11, wherein said oxidizable metal ion is copper ion.

13. The process of claim 12, wherein the adsorption step is carried out at a temperature between about 100° and about 200° C.

14. The process of claim 10, wherein said adsorbent is type 4A zeolite.

15. The process of claim 14, wherein said adsorbent contains exchangeable cations other than sodium ions, but at a level insufficient to divest the adsorbent of its type 4A character.

16. The process of claim 14, wherein the adsorption step is carried out at a temperature in the range of about 50° to about 200° C. and an absolute pressure in the range of about 0.2 to 100 bar.

17. The process of claim 14, wherein the adsorption step is carried out at a temperature in the range of about 70° to about 170° C. and an absolute pressure of about 1 to 50 bar.

18. The process of claim 1 or claim 7, wherein the adsorption and regeneration steps comprise a pressure swing adsorption cycle.

19. The process of claim 7, wherein step (d) is carried out by flashing unreacted propylene and propane from said product stream.

20. The process of claim 7, wherein step (d) is carried out by stripping unreacted propylene and propane from said product.

21. The process of claim 7, wherein step (d) is carried out by first flashing unreacted propylene and propane from said product stream and then stripping unreacted propylene and propane from said product stream.

22. The process of claim 7, further comprising, prior to step (d), the step of separating from said product stream a gas stream containing at least one member selected from carbon monoxide and hydrogen.

23. The process of claim 1 or claim 7, wherein the adsorption step is carried out at a temperature in the range of about 50° to about 200° C. and an absolute pressure in the range of about 0.2 to 20 atmospheres.

24. The process of claim 1 or claim 7, wherein the adsorption and regeneration steps comprise a pressure swing adsorption cycle.

25. The process of claim 24, wherein the adsorbent is at least partly regenerated by countercurrent depressurization.

26. The process of claim 25, wherein the adsorption step is carried out at a temperature in the range of about 70° to about 170° C. and an absolute pressure of about 1 to 10 atmospheres.

27. The process of claim 25, wherein the zeolite type 4A is further regenerated by depressurization to subatmospheric pressure by means of vacuum.

28. The process of claim 25, wherein the zeolite type 4A is further regenerated by purging the bed with an inert gas, the nonadsorbed product gas, the desorbed product gas or combinations of these.

29. The process of claim 1 or claim 7, wherein said oxo product is selected from butyraldehyde, n-butyl alcohol and mixtures of these.

* * * * *